United States Patent [19]
Kenosh

[11] Patent Number: 6,083,184
[45] Date of Patent: *Jul. 4, 2000

[54] ANKLE ORTHOTIC

[76] Inventor: Michael J. Kenosh, 96 Holden Rd., North Chittenden, Vt. 05763

[*] Notice: This patent is subject to a terminal disclaimer.

[21] Appl. No.: 09/157,211

[22] Filed: Sep. 18, 1998

Related U.S. Application Data

[63] Continuation of application No. 08/801,840, Feb. 14, 1997, Pat. No. 5,810,754.

[51] Int. Cl.[7] ........................................ A61F 5/00
[52] U.S. Cl. ................................ 602/27; 602/6
[58] Field of Search ............................ 602/5, 6, 23, 27, 602/29; 36/89, 117.1, 118.2, 119.1; D24/192

[56] References Cited

U.S. PATENT DOCUMENTS

| | | | |
|---|---|---|---|
| Re. 33,395 | 10/1990 | Peters | 128/80 |
| D. 255,384 | 6/1980 | Finnieston | D24/192 |
| D. 345,421 | 3/1994 | Schumann | D24/192 |
| 4,934,355 | 6/1990 | Porcelli | 128/80 |
| 4,960,135 | 10/1990 | Nelson | 128/80 |
| 4,982,733 | 1/1991 | Broadhurst et al. | 128/804 |
| 5,007,417 | 4/1991 | Bender | 128/80 |
| 5,031,607 | 7/1991 | Peters | 128/80 |
| 5,038,762 | 8/1991 | Hess et al. | 128/80 |
| 5,050,620 | 9/1991 | Cooper | 128/80 |
| 5,056,509 | 10/1991 | Swearington | 128/80 |
| 5,069,202 | 12/1991 | Prock | 128/80 |
| 5,176,623 | 1/1993 | Stetman et al. | 602/27 |
| 5,199,941 | 4/1993 | Makinen | 602/27 |
| 5,209,722 | 5/1993 | Miklaus et al. | 602/27 |
| 5,213,564 | 5/1993 | Johnson et al. | 602/27 |
| 5,217,431 | 6/1993 | Toronto et al. | 602/27 |
| 5,219,324 | 6/1993 | Hall | 602/28 |
| 5,226,875 | 7/1993 | Johnson | 602/27 |
| 5,250,021 | 10/1993 | Chang | 602/27 |
| 5,271,418 | 12/1993 | Ohnuma et al. | 128/882 |
| 5,352,189 | 10/1994 | Schumann et al. | 602/23 |
| 5,376,068 | 12/1994 | Grifka | 602/27 |
| 5,389,065 | 2/1995 | Johnson, Jr. | 602/27 |
| 5,430,960 | 7/1995 | Richardson | 36/89 |
| 5,445,602 | 8/1995 | Grim et al. | 602/27 |
| 5,445,603 | 8/1995 | Wilkerson | 602/27 |
| 5,449,005 | 9/1995 | Echols | 128/882 |
| 5,472,414 | 12/1995 | Detty | 602/27 |
| 5,475,935 | 12/1995 | Frost | 36/89 |
| 5,496,263 | 3/1996 | Fuller, II et al. | 602/27 |
| 5,527,269 | 6/1996 | Reithofer | 602/27 |
| 5,584,799 | 12/1996 | Gray | 602/5 |
| 5,697,893 | 12/1997 | Rhenter | 602/27 |
| 5,810,754 | 9/1998 | Kenosh | 602/27 |
| 5,971,946 | 10/1999 | Quinn et al. | 602/27 |

*Primary Examiner*—Richard J. Apley
*Assistant Examiner*—Denise Pothier
*Attorney, Agent, or Firm*—James P. Murphy; McAndrews, Held & Malloy, Ltd.

[57] ABSTRACT

An ankle orthotic of substantially resilient material is provided comprised of a heel portion, an ankle support portion, and a talofibular support portion. The heel portion is substantially rigid and form fitting, preventing excessive inversion forces from being generated at the subtalar joint. The ankle support portion is relatively resilient and extends vertically from the heel portion, with the medial aspect extending higher than the lateral aspect. This form results in creating a three-point pressure system, which resists inversion forces from displacing the ankle mortise. The proximal end of the ankle support portion is enclosed via a fastening strap to customize fit. The talofibular support portion extends laterally and distally from the heel portion and reinforces the relatively vulnerable anterior talofibular ligament, providing stabilization and decreasing injury to the lateral ligamentous complex of the ankle.

A flange or similar device may be present on the heel and/or forefoot of the orthotic allowing incorporation into the body or last of a shoe. This exoskeletal design would allow maximal structural stability by decreasing shear forces which might form between the shoe/orthotic interface.

14 Claims, 7 Drawing Sheets

ANKLE ORTHOTIC

This application is a continuation of my prior, copending application Ser. No. 08/801,840, filed on Feb. 14, 1997, now U.S. Pat. No. 5,810,754.

BACKGROUND OF THE INVENTION

The human ankle joint is a complex structure of bone, muscle, and connective tissue which is subject to tremendous physical stress in everyday and sporting activities. As a result of its inherent architecture, the ankle joint, or "mortise", is extremely stable to eversion forces which produce a rolling inward onto the medial, or inside portion of the ankle and foot. This stability, however, is sacrificed on the lateral, or outside portion of the joint, which has less bony reinforcement and weaker ligaments. Ankle inversion injuries, or sprains, typically describe a rolling outward onto the lateral aspect of the ankle and foot. This common injury frequently damages the anterior talofibular ligament, which has the unenviable task of reinforcing the anterolateral aspect of the mortise. As a consequence, permanent instability of the ankle may result.

Several types of ankle braces exist to support the ankle post-injury, but little has been done prophylactically to prevent these injuries. Most devices currently available can be bulky, uncomfortable, and expensive. Furthermore, they are not based on any biomechanical principles, which limits their ankle support function.

SUMMARY OF THE INVENTION

The present invention relates to an ankle orthotic and prophylactic device that provides a new, unique approach to complete ankle support, especially for the athlete or person involved in rigorous activity. This device would as well be appropriate for individuals who have previously suffered ankle sprains, as they are statistically at higher risk for recurrent injury and prolonged morbidity.

The ankle orthotic of the present invention is comprised of three distinct parts: A heel portion, or counter, which substantially surrounds the heel of the foot, or calcaneus; the ankle support portion, which extends vertically from either side of the heel counter and is anatomically contoured along the lower leg, or distal tibia; and lastly, the talofibular support portion, which extends horizontally from the lateral portion of the heel counter near the lateral malleolus to a location terminating near the fifth metatarsal head.

The heel counter of the orthotic of the present invention is relatively rigid, and ensures a comfortable, secure fit while maintaining the subtalar joint in a neutral position. The subtalar joint provides the ankle with a considerable amount of inversion and eversion range of motion, and the counter acts to control the calcaneus and hindfoot against excessive inversion experienced during the ankle sprain. The end result is a decrease in the forces leading to a strain of the lateral ligamentous complex of the ankle, which includes the anterior talofibular ligament. The heel counter also acts to anchor and bridge the ankle support and talofibular support portions of the present orthotic.

The medial aspect of the ankle support portion extends vertically further than the lateral portion and employs a three-point pressure system to disperse inversion forces which originate from the lower leg. This control system is a classic principle of biomechanics proven in contemporary spine, knee, and finger bracing. It increases support across the ankle mortise while preserving the mobility necessary for athletic activities or similarly rigorous work. The ankle support portion preferentially includes a Velcro® or similar fastening strap to secure around the leg.

The talofibular support portion extends around the lateral side of the foot at a location intermediate between the lateral malleolus and the fifth metatarsal head. It significantly stabilizes and reinforces the anterior talofibular ligament, which is the most commonly injured ligament of the lateral ligamentous complex during an ankle sprain, secondary to its vulnerability with the foot in a flexed, inverted posture.

Thus, an object of the present invention is to provide an ankle orthotic which helps prevent rollover and inversion sprains by stabilizing the ankle mortise and subtalar joint, as well as reinforcing the anterior talofibular ligament, during rigorous physical activities to help prevent injuries.

Another object of the present invention is to provide an ankle orthotic which significantly protects the ankle joint after an inversion injury.

Another object of the present invention is to provide an exoskeletal orthotic which can potentially be incorporated into the last of a shoe, providing maximum stability by reducing any shear forces which might result between an orthotic/shoe interface.

A still further object of the present invention is to provide a lightweight ankle orthotic which can be worn independently inside a shoe.

An even further object of the present invention is to provide a lightweight inexpensive ankle orthotic, based on proven biomechanical principles, which can be economically manufactured.

DETAILED DESCRIPTION OF THE PREFERRED EMBODIMENTS

Figure 1:
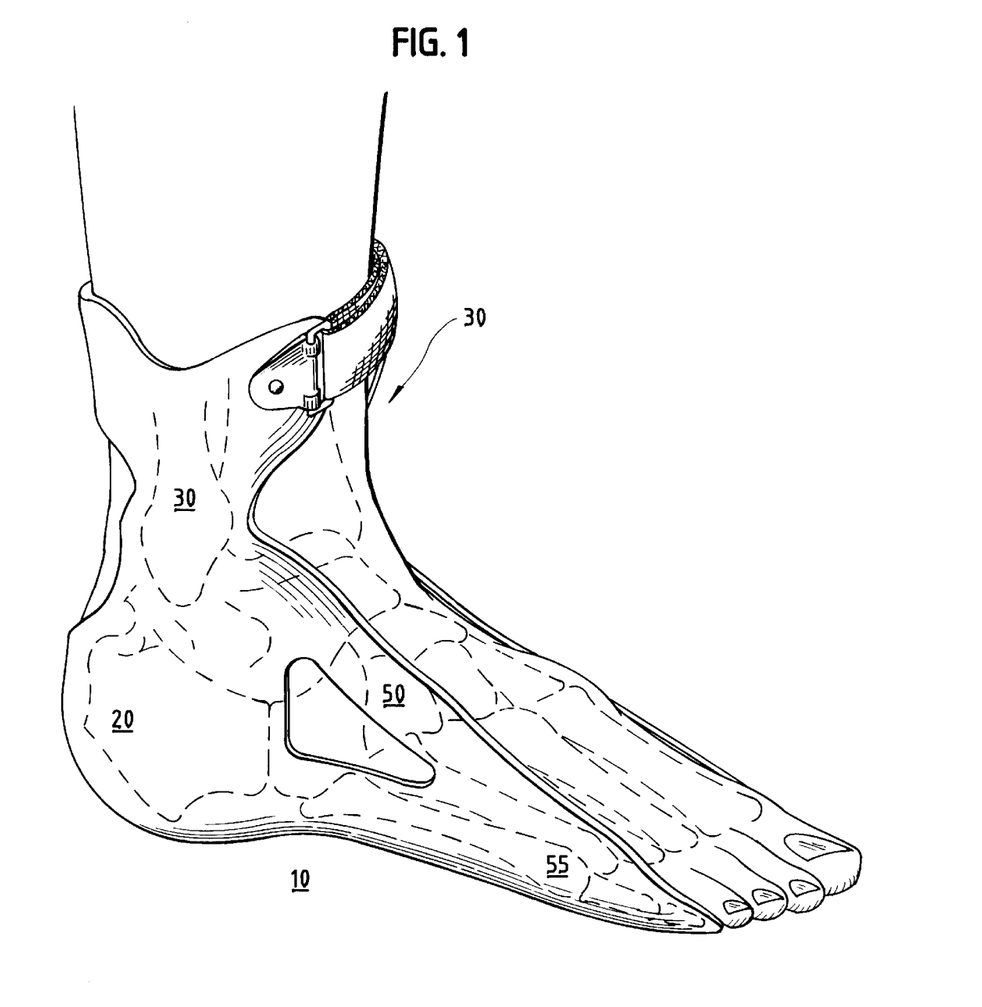
FIG. 1 is a perspective view of the present invention being worn on the right ankle, with the bony architecture of the foot provided in relief.
Figure 2:
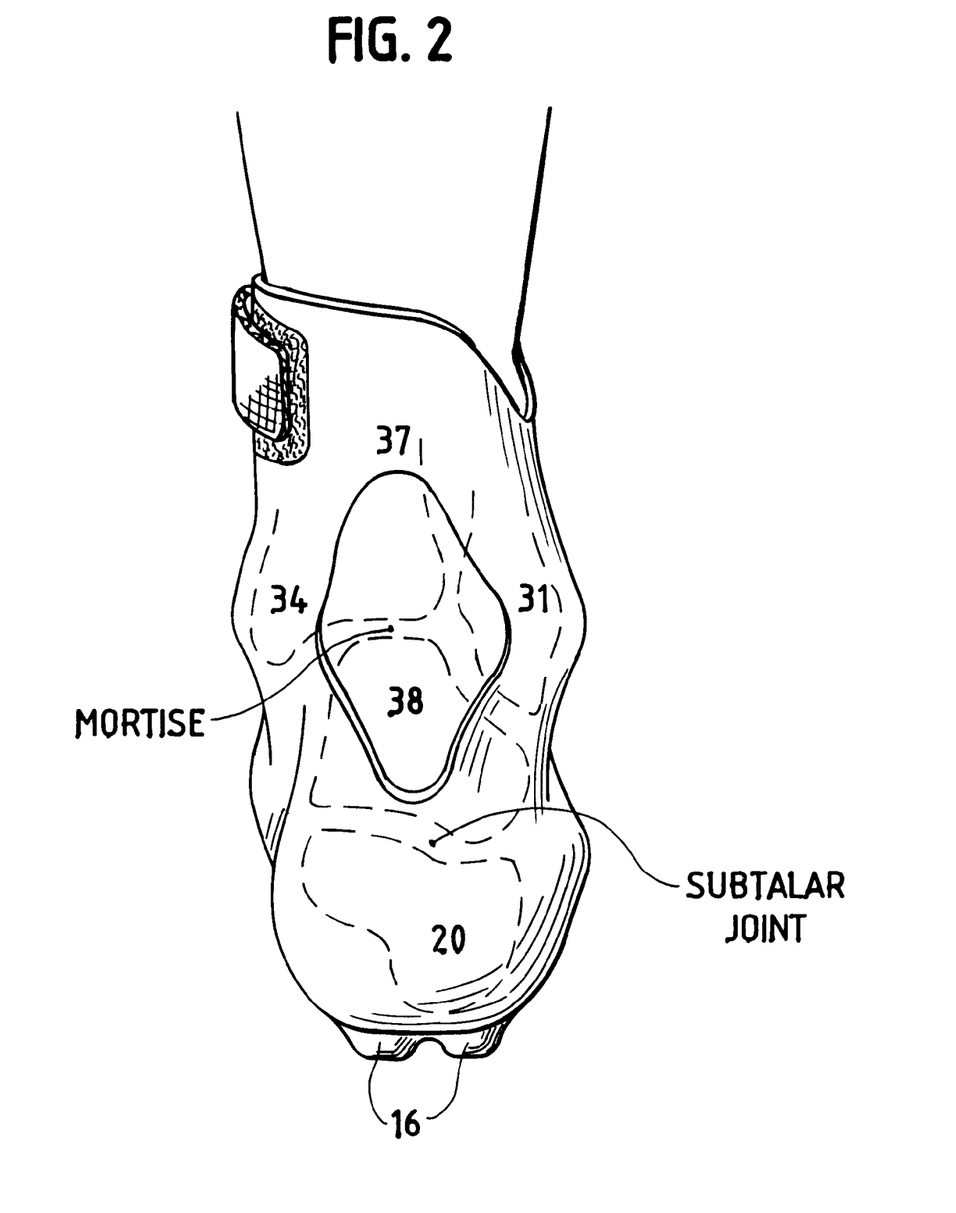
FIG. 2 is a rear view of the present invention being worn on the right ankle, with the bony architecture of the foot provided in relief.

As seen in FIGS. 1 and 2, and designated generally 10 in FIG. 1, the present ankle orthotic invention is worn on the foot and ankle to provide support in strenuous activities and prevent injuries; specifically ankle inversion sprains or rollover injuries onto the lateral foot. This injury commonly occurs when the foot is in a plantarflexed posture (toes pointing down), such as when returning to the ground after a jump. If a force or object should act on the foot and ankle at that time, providing an inversion moment on the hindfoot, significant ligamentous injury may result. Ankle orthotic 10 includes a heel portion 20, an ankle support portion 30, and a talofibular support portion 50.

Figure 2A:
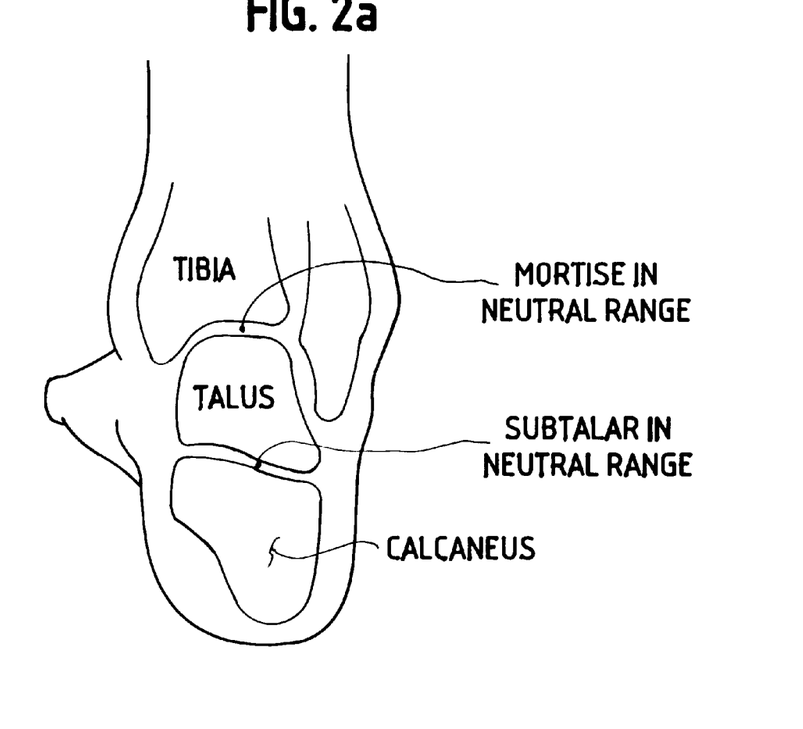
FIG. 2a is a rear view cross section of the right foot and ankle outlining the subtalar joint and ankle mortise at their respective neutral ranges of motion.
Figure 2B:
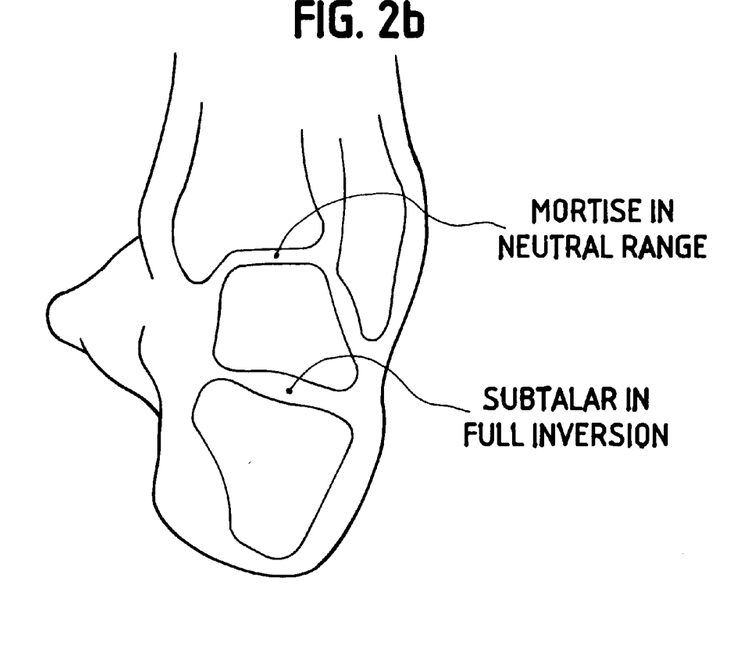
FIG. 2b is a rear view cross section of the right foot and ankle outlining the subtalar joint in normal full inversion, and the ankle mortise in normal neutral range.

Heel portion 20 substantially surrounds the heel, or calcaneus, of the human foot. This design serves to stabilize the subtalar joint, as shown in FIGS. 2, 2a and 2b. While inversion and eversion describe normal range of motion at the subtalar joint, they do not occur at the ankle mortise except in injury. Failure to allow inversion to start at the mortise is crucial in preventing excessive forces from displacing this joint in a typical sprain. Heel portion 20 provides the rigid framework necessary to prevent development of said excessive forces.

Extending vertically from heel portion 20 is ankle support portion 30. (FIG. 1). Ankle support portion 30 includes medial portion 34, lateral portion 31, and posterior portion 37. (FIG. 2). Medial portion 34 extends vertically from heel portion 20 on the inside of the leg. Lateral portion 31 extends vertically from heel portion 20 on the outside of the leg. Posterior portion 37 extends upward from heel portion 20. As seen in FIG. 2, the preferred embodiment includes aperture 38 in posterior section 37 to decrease the weight of orthotic 10. Ankle support portion 30 is substantially U-shaped in horizontal cross section to cover and support both sides and the back of the leg above the ankle.

Figure 3:
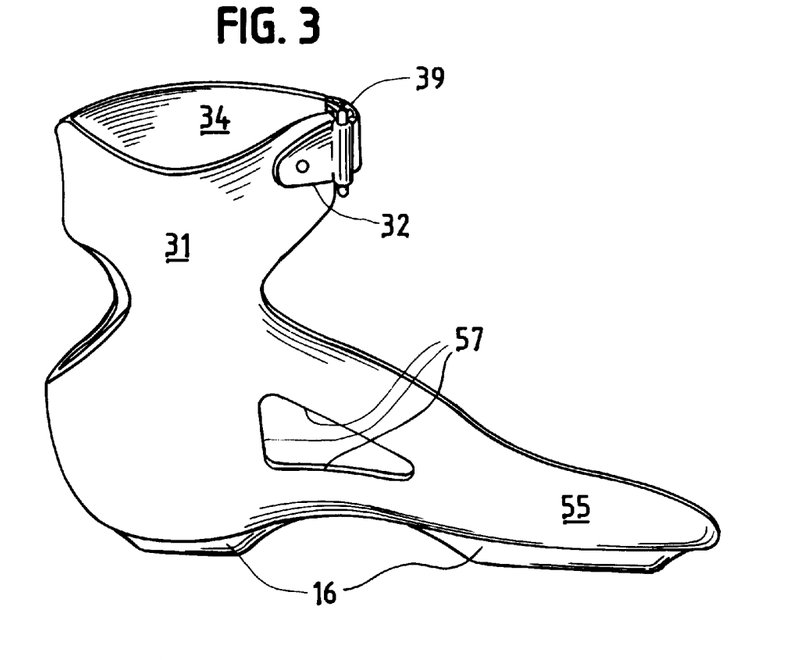
FIG. 3 is a right side view of the ankle orthotic of the present invention.
Figure 4:
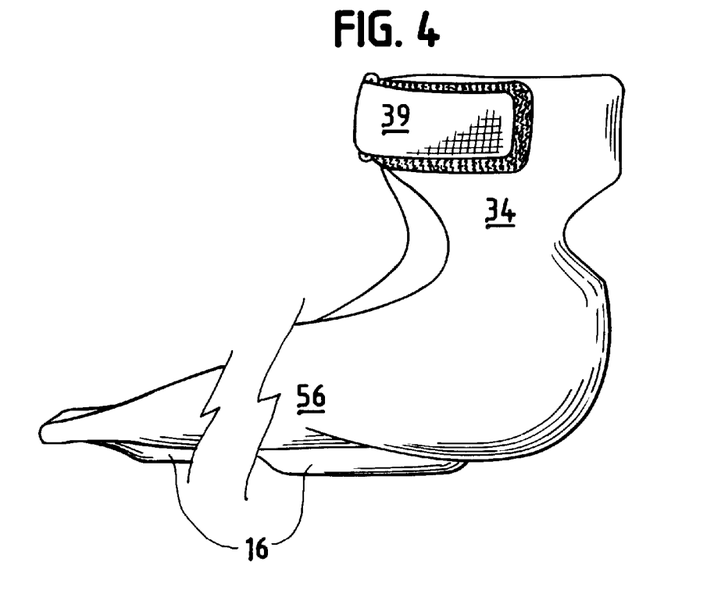
FIG. 4 is a left side partial cutaway view of the ankle orthotic of the present invention.

At the proximal anterior aspect of ankle support portion 30 is fastening strap 39. Fastening strap 39 is preferentially a Velcro® strap affixed to medial portion 34 and a buckle 32, or similar device, affixed to lateral portion 31. Fastening strap 39 provides extra support for orthotic 10 by customizing the fit against the distal leg and ankle. (FIGS. 3 and 4).

Figure 5:
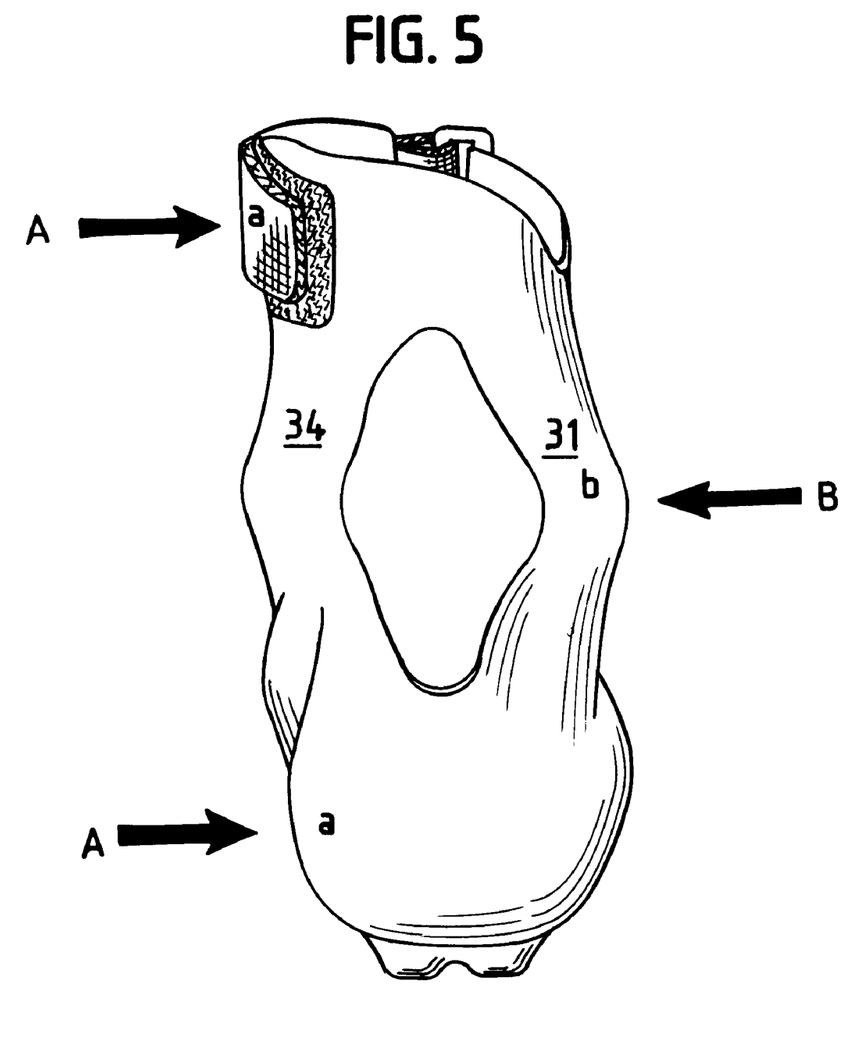
FIG. 5 is a rear view cross section of the foot and ankle with vector analysis of the action of the three-point pressure system.

Medial portion 34 of ankle support portion 30 extends vertically further than lateral portion 31. As best seen in FIGS. 2 and 3, this allows greater flexibility of orthotic 10 while preserving its attendant benefits of supporting the ankle and preventing an inversion sprain. This design also provides a three-point pressure system as shown by points a and b in FIG. 5. This three-point pressure system provides increased stabilization at the ankle mortise by utilizing two medial pressure points, a, which are balanced by a third opposing lateral pressure point, b. If inversion forces are generated at the subtalar joint, the three-point system will disperse their ability to act on and displace the mortise. The force vectors, shown as arrows A and B, which allow this system to work are displayed in FIG. 5.

Orthotic 10 is ergonomically contoured and preferentially manufactured of modified polyethylene, or similar thermosetting material, to provide resiliency and strength simultaneously. The modified polyethylene allows orthotic 10 to be sufficiently resilient to accommodate intended motion of the ankle and foot, but provides excellent stabilization against inversion. Because, as shown in its preferred embodiment, ankle support portion 30 is narrow near the ankle mortise on medial portion 34 and lateral portion 31, orthotic 10 can flex and extend in the vertical, longitudinal plane of the foot, allowing normal activities such as running and jumping. However, in a lateral rollover or inversion trauma situation, the ankle support portion significantly reduces pathologic forces at the ankle mortise as a result of the three-point pressure system previously described, thereby reducing the magnitude of injury.

Figure 6:
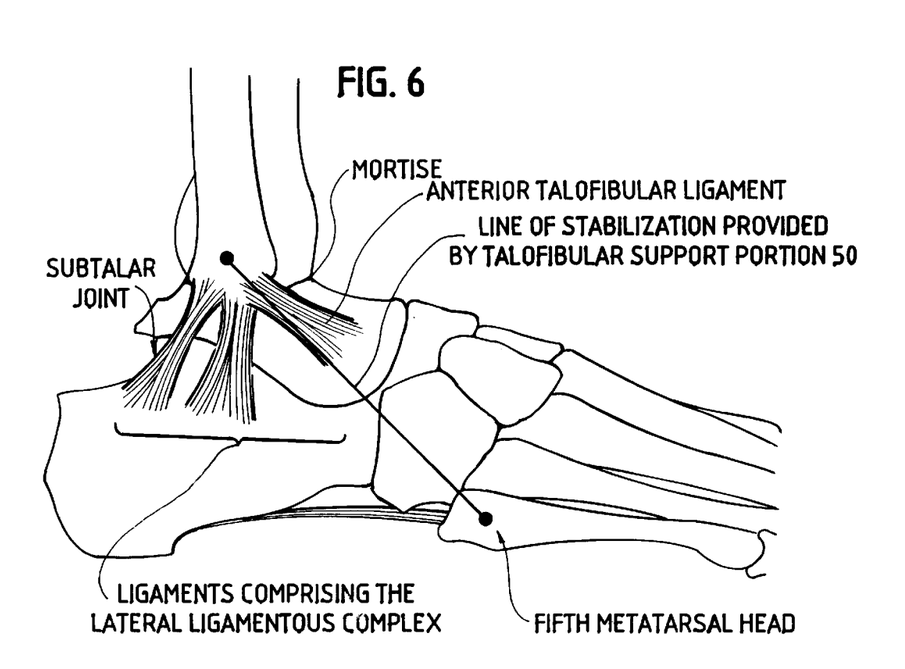
FIG. 6 is a lateral view of the anatomy of the right foot and ankle.
Figure 7:
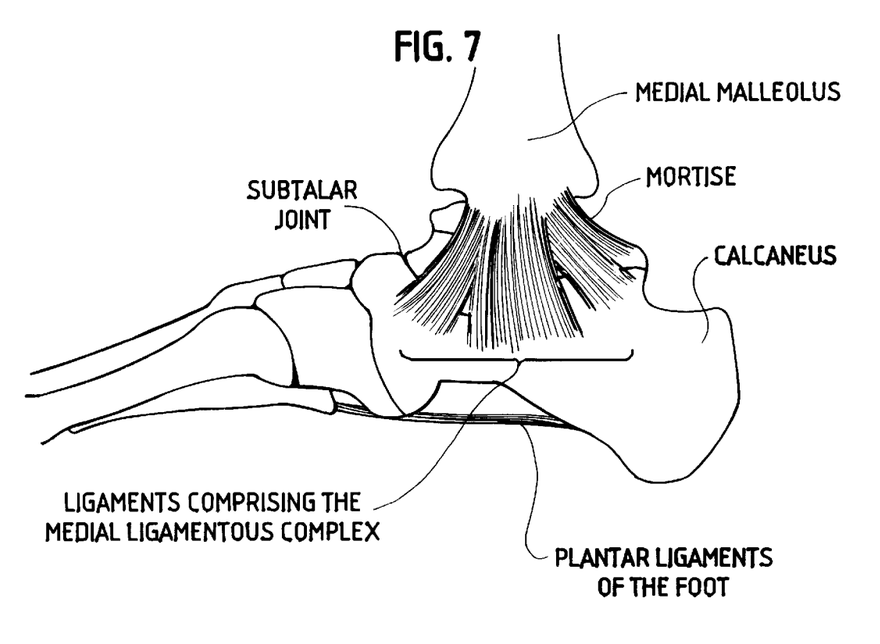
FIG. 7 is a medial view of the anatomy of the right foot and ankle.
Figure 8:
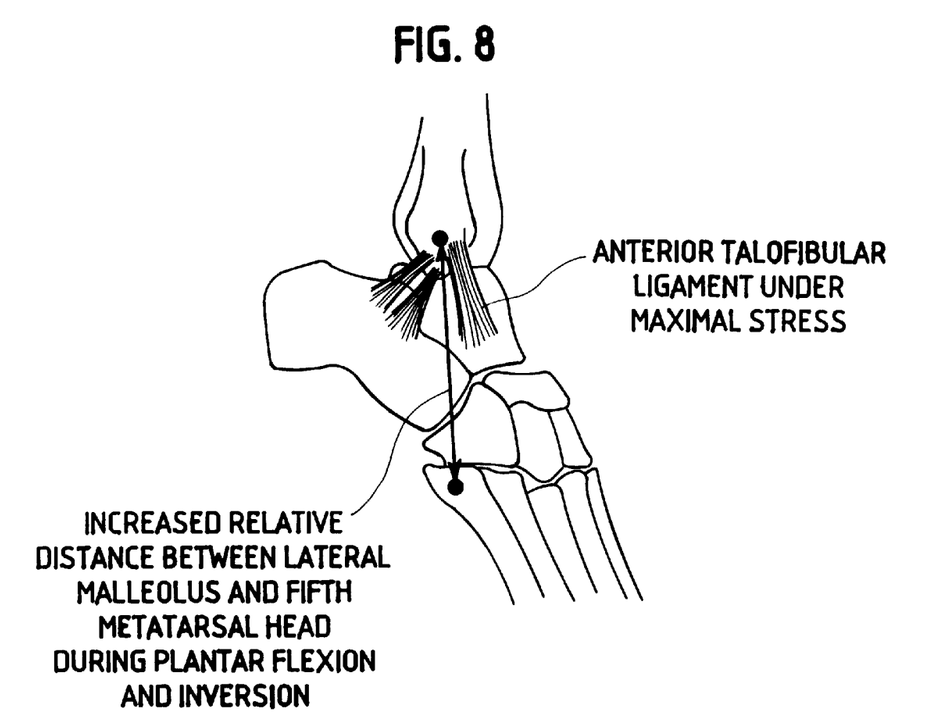
FIG. 8 is a depiction of anterior talofibular injury secondary to an inversion of the foot in a plantarflexed position.

The difference in stability of the medial versus lateral ligamentous complex is illustrated in FIGS. 6 and 7. The ligaments which form the medial group are often interdigitated into one large confluent structure, which allows greater tensile strength. The lateral ligamentous group is neither as contiguous or strong as the medial ligamentous complex, and is actually divided into individual bands. As a result, the lateral complex is weaker and more prone to injury. When involved in jumping and landing activities, the foot can land in a plantarflexed position as seen in FIG. 8, with the medial sole of the foot inverted above the lateral sole, such as when an obstacle resides under the medial side. When this occurs, the forces applied to the mortise may stretch the lateral ligaments past their intended limits. Secondary to plantarflexion, the anterior talofibular ligament is already stretched maximally. The added insult of inversion often increases this distraction, widening the relative distance between the lateral malleolus of the fibula and the fifth metatarsal head, resulting in ligamentous tear or rupture and subsequent instability (see FIG. 8). Orthotic 10, with all of its inherent parts, significantly reduces the chances of overstretching these ligaments when worn in the appropriate fashion.

Ankle orthotic 10 of the present invention further includes talofibular support portion 50. This section extends from ankle support portion 30 to forward section 55 at a point intermediate between the lateral malleolus of the fibula and the fifth metatarsal head, or area commonly referred to as the "ball" of the foot. (FIG. 1). Talofibular support portion 50 is superimposed over the anterior talofibular ligament, as shown in FIG. 1. It has been found that stress on the anterior talofibular ligament can be reduced by minimizing the relative distance and separation between the lateral malleolus and the fifth metatarsal head. Talofibular support portion 50 accomplishes this by providing a rigid block to overstretching in this plane, thereby protecting the ligament.

Aperture 57 on the lateral aspect of orthotic 10 assists in decreasing the overall weight of said invention while simultaneously defining the borders of previously described talofibular support portion 50. (FIG. 3). This design adds to the ability of the foot to move freely in a vertical, longitudinal plane, while still maintaining its anti-inversion properties. In the preferred embodiment, the talofibular support portion 50 is continuous in structure with the rest of ankle orthotic 10. An appropriately rigid material, however, could be attached to an orthotic at the same points of origin and insertion of the talofibular support portion and theoretically serve the same function.

On the medial aspect of ankle orthotic 10, the soleplate 56 rises sufficiently into the midfoot area to support the arch of the foot. (FIG. 4). In athletic activities and rigorous work, severe forces are often transmitted to the arch and metatarsal heads, which may result in inflammation of the plantar ligaments of the foot (seen in FIGS. 6 and 7). Plantar fasciitis or bone spurs on the heel may result from these severe repetitive forces. The medial soleplate and arch support dampen these forces and the strain they transmit to the plantar ligaments of the foot. The medial aspect of ankle orthotic 10 also serves to capture the medial aspect of the first metatarsal bone, in essence locking the orthotic onto the foot and ensuring maximum contact and functional stability.

For all aforementioned reasons, ankle orthotic 10 also serves to stabilize a foot which has been rendered unstable secondary to previous injury and ligamentous damage. The injured foot may then substitute ankle orthotic 10 for its lost protective mechanisms.

It is also envisioned that said invention may serve as an exoskeletal structure directly incorporated into the body or last of a shoe. In such an embodiment, a flanged section 16 would extend from heel portion 20 and forefoot portion 55 to fit directly into a corresponding receptacle of the shoe as seen in FIGS. 2, 3 and 4. A rigid attachment would diminish the possibility of shear forces developing between the orthotic/shoe interface. Although the orthotic would work sufficiently without attachment, the interface would allow even increased biomechanical support and function.

It will be appreciated by those skilled in the art that various changes and modifications can be made to the illustrated embodiments without departing from the spirit of the present invention. All such modifications and changes are intended to be covered by the appended claims.

What is claimed is:

1. A one-piece ankle orthotic to be worn on a human foot comprising:
   a heel portion adapted to abut and substantially surround the heel of a foot;
   an ankle support portion having a medial section and a lateral section extending vertically from the heel portion adapted to terminate at a position above the ankle of the user and below the knee of the user, and wherein the medial section extends further vertically than the lateral section to establish a three-point pressure system;
   a talofibular support portion adapted to extend distally toward the toes of the foot of the user from the heel portion and adapted to reinforce the anterior talofibular ligament of the user;
   wherein said medial and lateral sections provide ankle support when worn on a foot to resist rollover and inversion injuries, and said talofibular support portion helps to stabilize the anterior talofibular ligament of the user thereby reducing the risk of ankle injury or recurrent damage to a previously injured or unstable ankle.

2. The ankle orthotic of claim 1 wherein said heel portion includes a flange allowing incorporation of said orthotic into body or last of a shoe in an exoskeletal manner.

3. The ankle orthotic of claim 1 wherein said talofibular support portion includes a flange allowing incorporation of said orthotic into the body or last of a shoe in an exoskeletal manner.

4. The ankle orthotic of claim 1 wherein said orthotic is made of a substantially resilient material.

5. The ankle orthotic of claim 4 wherein said substantially resilient material is modified polyethylene.

6. The ankle orthotic of claim 1 wherein the ankle support portion has a proximal end at a location furthest from said heel portion and further comprising a fastener attached to the proximal end of said ankle support portion to secure said orthotic to the leg of a user.

7. The ankle orthotic of claim 6 wherein the fastener comprises a buckle and a strap.

8. The ankle orthotic of claim 1 wherein the talofibular support portion further comprises an arch support surface adapted to extend vertically to abut the arch of the foot of the wearer and assist to ameliorate stress to the plantar ligaments of the foot.

9. The ankle orthotic of claim 1 wherein said talofibular support portion includes a flange allowing incorporation of said orthotic into the body and last of a shoe.

10. A one-piece ankle orthotic comprised of substantially resilient material to be worn on a human foot comprising:
    a heel portion adapted to abut and substantially surround the heel of a foot;
    an ankle support portion having a medial section and a lateral section extending vertically from the heel portion adapted to terminate at a position above the ankle of the user and below the knee of the user, and wherein the medial section extends further vertically than the lateral section to establish a three-point pressure system;
    a talofibular support portion adapted to extend distally toward the toes of the foot of the user from the heel portion and having a lateral extension adapted to extend from an underside of the foot to above the foot and adapted to reinforce the anterior talofibular ligament of the user;
    wherein said medial and lateral sections provide ankle support when worn on a foot to resist rollover and inversion injuries, and said talofibular support portion helps to stabilize the anterior talofibular ligament of the user thereby reducing the risk of ankle injury or recurrent damage to a previously injured or unstable ankle.

11. The ankle orthotic of claim 10 wherein said heel portion includes a flange allowing incorporation of said orthotic into body or last of a shoe in an exoskeletal manner.

12. The ankle orthotic of claim 10 wherein the ankle support portion has a proximal end at a location furthest from said heel portion and further includes a fastener attached to the proximal end of said ankle support portion to secure said orthotic to the leg of a user.

13. The ankle orthotic of claim 10 wherein the talofibular support portion further comprises an arch support surface adapted to extend vertically to abut the arch of the foot of the wearer and assist to ameliorate stress to the plantar ligaments of the foot.

14. The ankle orthotic of claim 10 wherein said talofibular support portion includes a flange allowing incorporation of said orthotic into the body and last of a shoe.

\* \* \* \* \*